(12) United States Patent
Mou et al.

(10) Patent No.: US 10,663,387 B2
(45) Date of Patent: May 26, 2020

(54) GAS DETECTING DEVICE

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 0 days.

(21) Appl. No.: 16/224,146

(22) Filed: Dec. 18, 2018

(65) Prior Publication Data

US 2019/0212242 A1 Jul. 11, 2019

(30) Foreign Application Priority Data

Jan. 8, 2018 (TW) .............................. 107100703 A

(51) Int. Cl.
*G01N 15/02* (2006.01)
*G01N 33/00* (2006.01)
(Continued)

(52) U.S. Cl.
CPC ........ *G01N 15/0211* (2013.01); *F04B 39/121* (2013.01); *F04B 39/123* (2013.01);
(Continued)

(58) Field of Classification Search
CPC .. G01N 15/0211; G01N 15/06; G01N 33/004; G01N 33/0047; G01N 2015/0019; G01N 2015/0693
(Continued)

(56) References Cited

U.S. PATENT DOCUMENTS 7,928,394 B1 4/2011 Richer
2002/0144537 A1 10/2002 Sharp et al.
(Continued)

FOREIGN PATENT DOCUMENTS

CN 204807134 U 11/2015
JP 2011-27079 A 2/2011
TW M525446 U 11/2015

OTHER PUBLICATIONS

Extended European Search Report, dated May 10, 2019, for European Application No. 18213447.8.

*Primary Examiner* — Isiaka O Akanbi
(74) *Attorney, Agent, or Firm* — Birch, Stewart, Kolasch & Birch, LLP

(57) ABSTRACT

A gas detecting device is disclosed and comprises a main body, a suspended particle sensing module and a gas sensing module, wherein the main body includes a first sensing area and a second sensing area. A suspended particle sensing module disposed within the first sensing area includes an irradiating mechanism, a first gas transporting actuator, a laser device and a light sensing device. The first gas transporting actuator transmits air to the first sensing area, the suspended particles in the air is irradiated by the laser beam emitted from the laser device to generate scattered light spots for the light sensing device to detect the suspended particles. The gas sensing module disposed within the second sensing area includes a gas sensor and a second gas transporting actuator. The second gas transporting actuator transmits air to the second sensing area, and the gas sensing device detects a gas composition contained in the air.

19 Claims, 12 Drawing Sheets

(51) Int. Cl.
*F04B 39/12* (2006.01)
*G01N 15/14* (2006.01)
*G01N 15/00* (2006.01)
*F04B 45/047* (2006.01)
*G01N 15/06* (2006.01)

(52) U.S. Cl.
CPC .......... *F04B 45/047* (2013.01); *G01N 15/06* (2013.01); *G01N 15/1459* (2013.01); *G01N 33/004* (2013.01); *G01N 33/0031* (2013.01); *G01N 33/0032* (2013.01); *G01N 33/0037* (2013.01); *G01N 33/0047* (2013.01); *G01N 2015/0019* (2013.01); *G01N 2015/0046* (2013.01); *G01N 2015/0693* (2013.01); *G01N 2015/1486* (2013.01); *G01N 2015/1493* (2013.01)

(58) Field of Classification Search
USPC ........................................................ 356/638
See application file for complete search history.

(56) References Cited

U.S. PATENT DOCUMENTS

| | | | |
|---|---|---|---|
| 2003/0115975 A1* | 6/2003 | Saaski | G01N 1/2273 73/864.33 |
| 2006/0250606 A1 | 11/2006 | Kaye et al. | |
| 2008/0278725 A1 | 11/2008 | Unger | |
| 2010/0050750 A1* | 3/2010 | Saaski | G01N 1/2205 73/61.75 |
| 2014/0178220 A1 | 6/2014 | Fujisaki et al. | |
| 2017/0222123 A1 | 8/2017 | Chen et al. | |

\* cited by examiner

GAS DETECTING DEVICE

FIELD OF THE DISCLOSURE

The present disclosure relates to a gas detecting device, and more particularly to a gas detecting device having a gas transporting actuator for gas transportation.

BACKGROUND OF THE DISCLOSURE

Nowadays, the air pollution problems are becoming increasingly serious in our country and its neighboring regions. In particular, the concentration of fine suspended particles (e.g. Particulate Matter 2.5, PM 2.5) is often too high. Hence, the monitoring of the concentration of suspended particles in the air is getting attention. However, since the air flowing with the wind direction and the air volume is not quantitative and the air quality monitoring stations for detecting suspended particles are mostly fixed points, it is impossible to confirm the concentration of suspended particles in the current surroundings. Hence, a miniature portable gas detecting device is needed. It allows users to measure the concentration of suspended particles around the surrounding, anytime and anywhere.

Moreover, the conventional gas detecting devices are often only capable of detecting a single substance (e.g., suspended particles) in the air. However, in addition to the suspended particles described above, there are many gases harmful to the human body in daily life. It would influence the health of the human body if we don't detect the harmful gases and suspended particles simultaneously.

SUMMARY OF THE DISCLOSURE

A gas detecting device is provided to simultaneously measure a concentration of suspended particles and other gas concentrations in air, so as to provide a user with air information timely and accurately.

In accordance with an aspect of the present disclosure, there is provided a gas detecting device. The gas detecting device includes a main body, a suspended particle sensing module, and a gas sensing module. The main body includes a first sensing area and a second sensing area, wherein the first sensing area has a first inlet and a first outlet disposed thereon, and the second sensing area has a second inlet and a second outlet. The suspended particle sensing module is disposed in the first sensing area of the main body and includes an irradiating mechanism, a first gas transporting actuator, a laser device and a light sensing device, wherein the first gas transporting actuator transports air through the first inlet at high speed, suspended particles in the air are irradiated by laser beam emitted from the laser device to generate scattered light spots, and the scattered light spots are detected by the light sensing device to obtain sizes and a concentration of the suspended particles. The gas sensing module is disposed in the second sensing area of the main body and includes a gas sensor and a second gas transporting actuator, wherein the second gas transporting actuator transports air through the second inlet at high speed, and the gas sensor detects the air to obtain a concentration of a target gas contained in the air.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
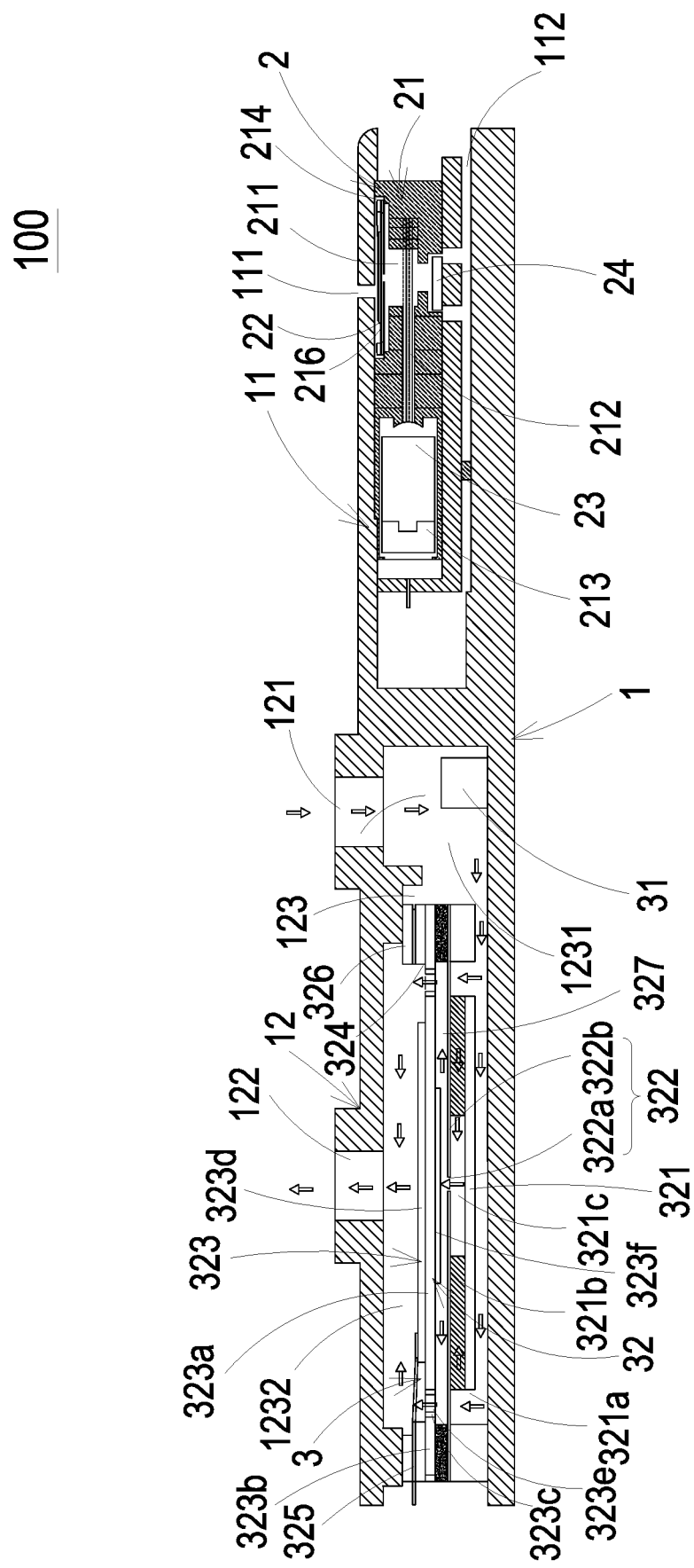
FIG. 1 is a schematic cross-sectional view illustrating a gas detecting device according to an embodiment of the present disclosure.

Please refer to FIG. 1. The present disclosure provides a gas detecting device 100 including at least one main body 1, at least one suspended particle sensing module 2, at least one gas sensing module 3, at least one first sensing area 11, at least one second sensing area 12, at least one first inlet 111, at least one first outlet 112, at least one second inlet 121, at least one second outlet 122, at least one irradiating mechanism 21, at least one first gas transporting actuator 22, at least one laser device 23, at least one light sensing device 24, at least one gas sensor 31 and at least one second gas transporting actuator 32. The numbers of the main body 1, the suspended particle sensing module 2, the gas sensing module 3, the first sensing area 11, the second sensing area 12, the first inlet 111, the first outlet 112, the second inlet 121, the second outlet 122, the irradiating mechanism 21, the first gas transporting actuator 22, the laser device 23, the light sensing device 24, the gas sensor 31 and the second gas transporting actuator 32 are exemplified by one for each respectively in the following embodiments but not limited thereto. It is noted that each of the main body 1, the suspended particle sensing module 2, the gas sensing module 3, the first sensing area 11, the second sensing area 12, the first inlet 111, the first outlet 112, the second inlet 121, the second outlet 122, the irradiating mechanism 21, the first gas transporting actuator 22, the laser device 23, the light sensing device 24, the gas sensor 31 and the second gas transporting actuator 32 can also be provided in plural numbers.

The gas detecting device 100 of the present disclosure is used to measure concentrations of suspended particles and gas information in the air. Please refer to FIG. 1, which is a schematic cross-sectional view illustrating a gas detecting device according to an embodiment of the present disclosure. In the embodiment, the gas detecting device 100 includes a main body 1, a suspended particle sensing module 2 and a gas sensing module 3. The main body 1 has a first sensing area 11 and a second sensing area 12. More specifically, the main body 1 has a top plate, a center pillar, and a bottom plate opposite to the top plate. The center pillar is connected between the top plate and the bottom plate, and divides the main body 1 into two parts, that is, the first sensing area 11 and the second sensing area 12. The first sensing area 11 is separated from the second sensing area 12 by the center pillar that makes the cross section of the gas detecting device 100 display an I-shaped profile. The first sensing area 11 has a first inlet 111 and a first outlet 112. The second sensing area 12 has a second inlet 121, a second outlet 122 and a detecting chamber 123. The detecting chamber 123 has an inlet channel 1231 and an outlet channel 1232. The inlet channel 1231 is aligned with the second inlet 121 and the outlet channel 1232 is aligned with the second outlet 122. The first inlet 111, the second inlet 121, and the second outlet 122 are disposed on the top plate. The first outlet 112 is disposed on a sidewall (not shown) of the main body 1 between the top plate and the bottom plate. The first inlet 111, the second inlet 121, and the second outlet 122 extend along a first direction, and the first outlet 112 extends along a second direction. The first direction is substantially perpendicular to the second direction. That is, the first inlet 111 and the first outlet 112 extend along different directions and are perpendicular to each other; the second inlet 121 and the second outlet 122 extend along the same direction and are parallel to each other; the first inlet 111 and the second inlet 121 extend along the same direction and are parallel to each other; the first outlet 112 and the second outlet 122 extend along different directions and are perpendicular to each other.

The suspended particle sensing module 2 is disposed in the first sensing area 11 of the main body 1 and includes has an irradiating mechanism 21, a first gas transporting actuator 22, a laser device 23 and a light sensing device 24. The irradiating mechanism 21 includes an airflow channel 211, a light-beam channel 212, a light-source receiving slot 213 and an accommodation slot 214. The airflow channel 211 is in fluid communication with the first inlet 111 and the first outlet 112. The light-beam channel 212 crosses through the airflow channel 211 and is adjacent to and in fluid communication with the light-source receiving slot 213. The accommodation slot 214 is disposed on one end of the airflow channel 211 and aligned with the first inlet 111. In addition, the first gas transporting actuator 22 is disposed within the accommodation slot 214 of the irradiating mechanism 21. When the first gas transporting actuator 22 is actuated, the air is inhaled through the first inlet 111 and introduced into the airflow channel 211. The laser device 23 is disposed within the light-source receiving slot 213 of the irradiating mechanism 21 and configured to emit a laser beam into the light-beam channel 212. The light sensing device 24 is disposed within the airflow channel 211 and corresponding to a position under the light-beam channel 212. When the first gas transporting actuator 22 is actuated, the air is inhaled through the first inlet 111 and introduced into the airflow channel 211. In the same time, the laser beam of the laser device 23 is emitted through the light-beam channel 212 to irradiate the air in the airflow channel 211, scattered light is generated by the suspended particles in the air, and the scattered light spots generated by the suspended particles are detected by light sensing device 24 disposed under the light-beam channel 212 to calculate accordingly the sizes and the concentration of the suspended particles contained in the air. The suspended particles detected can be for example suspended particles PM2.5 or suspended particles PM10.

The gas sensing module 3 is disposed in the second sensing area 12 of the main body 1 and includes a gas sensor 31 and a second gas transporting actuator 32. The gas sensor 31 is disposed in the inlet channel 1231 of the second sensing area 12, that is, on a bottom of the inlet channel 1231. The second gas transporting actuator 32 is fixed within the detecting chamber 123 and corresponding to the outlet channel 1232. In other words, the second gas transporting actuator 32 is aligned with the outlet channel 1232 and the second outlet 122. When the second gas transporting actuator 32 is actuated, the pressure in the interior of the detecting chamber 123 alters, and the air is inhaled through the second inlet 121 of the second sensing area 12 and introduced into the inlet channel 1231. The gas sensor 32 disposed in the inlet channel 1231 detects the air flowing through the inlet channel 1231 to measure the amount of a target gas contained in the air. The gas sensor 32 may measure one or more target gases contained in the air. In the embodiment, the gas sensor 31 can be one selected from the group consisting of an oxygen sensor, a carbon monoxide sensor, a carbon dioxide sensor and combinations thereof. In an embodiment, the gas sensor 31 can be a volatile organic compound sensor. Alternatively, the gas sensor 31 can be one selected from the group consisting of a bacterium sensor, a virus sensor, a microorganism sensor and combinations thereof.

Figure 2:
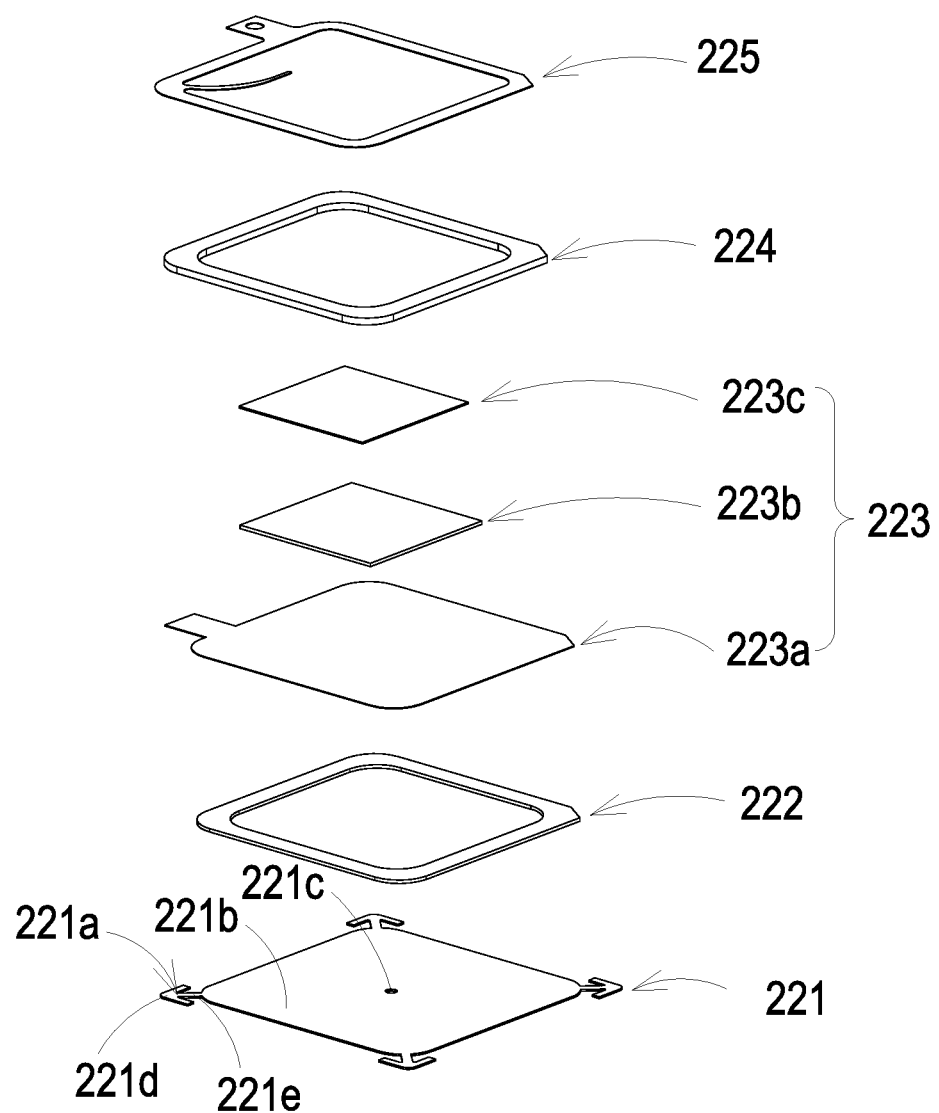
FIG. 2 is an exploded view illustrating the first gas transporting actuator of the present disclosure.
Figure 5A:
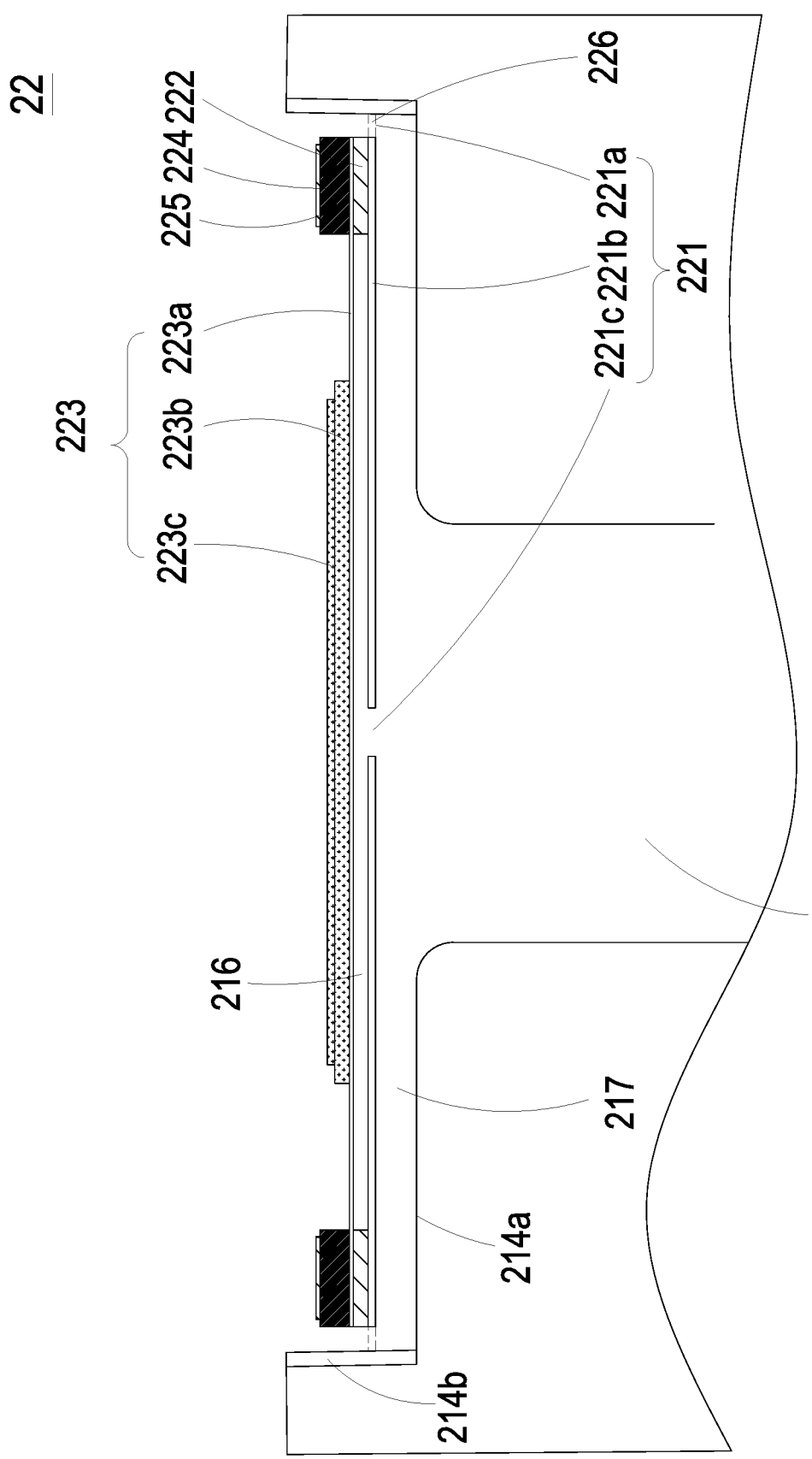
FIG. 5A is a schematic cross-sectional view illustrating the first gas transporting actuator of the present disclosure.

Please refer to FIGS. 1, 2 and 5A. FIG. 2 is an exploded view illustrating the first gas transporting actuator of the present disclosure, and FIG. 5A is a schematic cross-sectional view illustrating the first gas transporting actuator of the present disclosure. In the embodiment, the first gas transporting actuator 22 includes a gas transporting plate 221, a chamber connection component 222, an actuator 223, an insulation connection component 224 and a conducting connection component 225 stacked on each other sequentially. The gas transporting plate 221 includes a plurality of brackets 221a, a suspension plate 221b and a central aperture 221c. The suspension plate 221b is permitted to undergo a bending vibration. The plurality of brackets 221a are connected to the edge of the suspension plate 221b. In the embodiment, there are four brackets 221a, which are connected to four corners of the suspension plate 221b, respectively, but the present disclosure is not limited thereto. The central aperture 221c is formed at the center of the suspension plate 221b. The chamber connection component 222 is carried and stacked on the suspension plate 221b. The actuator 223 is carried and stacked on the chamber connection component 222 and includes a piezoelectric carrying plate 223a, an adjusting resonance plate 223b and a piezoelectric plate 223c. The piezoelectric carrying plate 223a is carried and stacked on the chamber connection component 222. The adjusting resonance plate 223b is carried and stacked on the piezoelectric carrying plate 223a. The piezoelectric plate 223c is carried and stacked on the adjusting resonance plate 223b. As the piezoelectric plate 223c is actuated by an applied voltage, the piezoelectric plate 223c deforms to drive the piezoelectric carrying plate 223a and the adjusting resonance plate 223b to bend and vibrate in the reciprocating manner. The insulation connection component 224 is carried and stacked on the piezoelectric carrying plate 223a of the actuator 223. The conducting connection component 225 is carried and stacked on the insulation connection component 224. A resonance chamber 216 is defined by the actuator 223, the chamber connection component 222 and the suspension plate 221b collaboratively. The adjusting resonance plate 223b is thicker than the piezoelectric carrying plate 223a.

Figure 3:
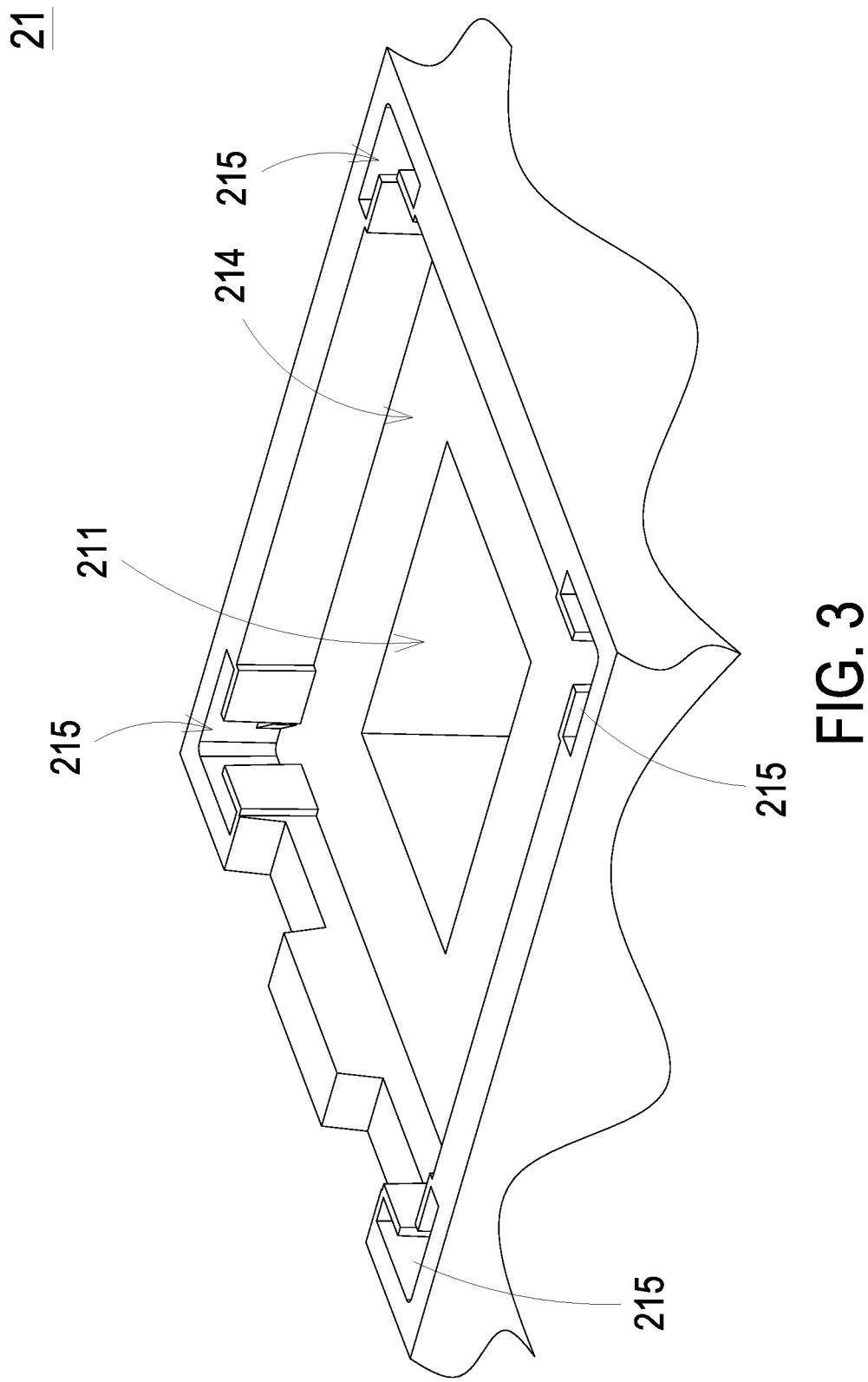
FIG. 3 is a schematic view illustrating the accommodation slot of the present disclosure.

Please refer to FIGS. 2, 3 and 5A, again. FIG. 3 is a schematic view illustrating the accommodation slot of the present disclosure. In the embodiment, each bracket 221a of the gas transporting plate 221 includes a fixing part 221d and a connection part 221e. The connection part 221e has an end connected to the suspension plate 221b and another end connected to the adjacent fixing part 221d. The accommodation slot 214 of the irradiating mechanism 21 has a bottom surface 214a and a lateral side 214b. The accommodation slot 214 has a plurality of fixing recesses 215 disposed therearound for receiving the fixing parts 221d of the brackets 221a. The shape of the fixing part 221d and the shape of the fixing recess 215 match each other. For example, the fixing part 221d is an L-shaped physical structure and the fixing recess 215 is an L-shaped recess. Fastened by the plurality of brackets 221a, the gas transporting plate 221 is received within the accommodation slot 214 and spaced apart from the bottom surface 214a of the accommodation slot 214, so that an airflow chamber 217 is formed between the suspension plate 221b and the bottom surface 214a of the accommodation slot 214. In addition, a plurality of vacant spaces 226 are formed among the suspension plate 221b, the plurality of brackets 221a and the lateral sides 214b of the accommodation slot 214.

Figure 4:
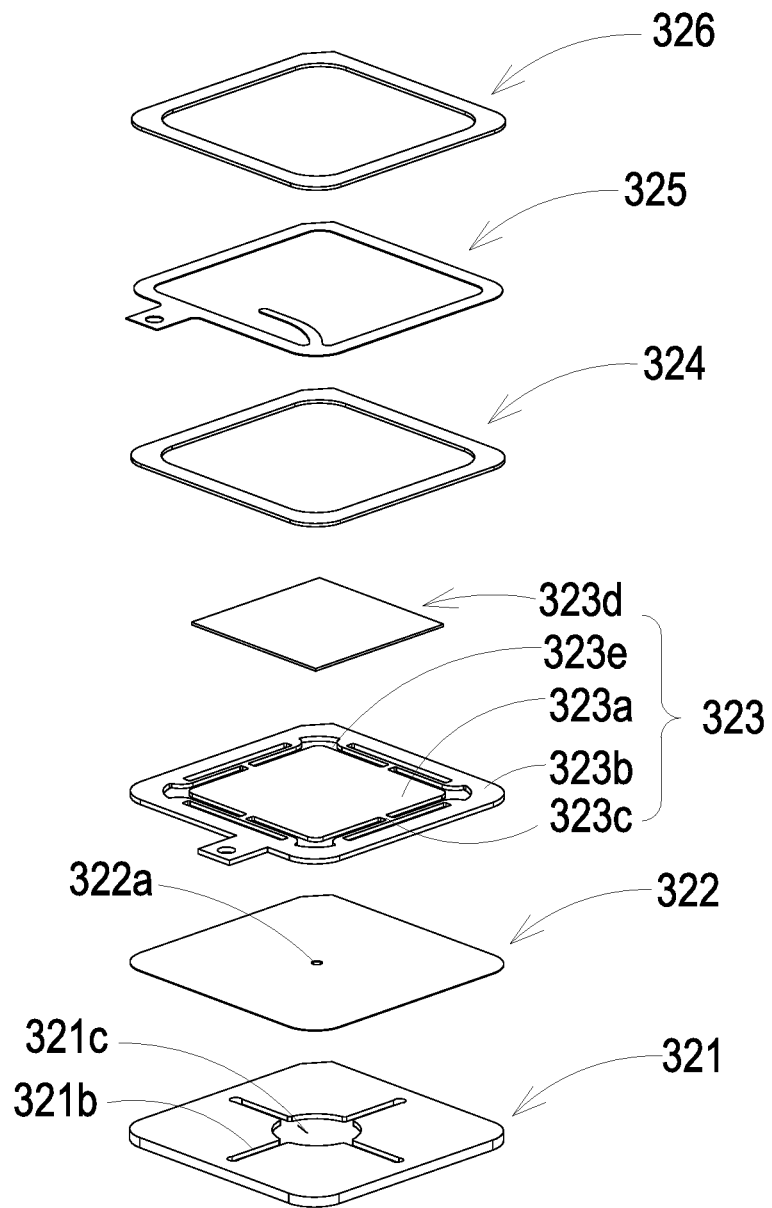
FIG. 4 is an exploded view illustrating the second gas transporting actuator of the present disclosure.

Please refer to FIGS. 1 and 4. FIG. 4 is an exploded view illustrating the second gas transporting actuator of the present disclosure. The second gas transporting actuator 32 includes an air inlet plate 321, a resonance plate 322, a piezoelectric actuator 323, a first insulation plate 324, a conducting plate 324 and a second insulation plate 326, which are stacked and assembled sequentially. The air inlet plate 321 includes at least one inlet 321a, at least one convergence channel 321b and a convergence chamber 321c. The convergence channel 321b is aligned with the inlet 321a. In the embodiment, the numbers of the inlets 321a and the convergence channels 321b are four, respectively, but not limited thereto. The convergence channel 321b has an end in fluid communication with the corresponding inlet 321a and another end in fluid communication with the convergence chamber 321c. The inlet 321a allows the air to flow in and the convergence channel 321b guides the air from the inlet 321a toward the convergence chamber 321c. The resonance plate 322 has a central aperture 322a and a movable part 322b. The central aperture 322a is vertically aligned with the convergence chamber 321c. The movable part 322b surrounds the central aperture 322a. The piezoelectric actuator 323 is aligned with the resonance plate 322 and includes a suspension plate 323a, an outer frame 323b, at least one connection component 323c and a piezoelectric element 323d. The outer frame 323b is arranged around the suspension plate 323a. The connection component 323c is connected between the outer frame 323b and the suspension plate 323a for elastically supporting the suspension plate 323a. Moreover, at least one vacant space 323e is formed among the connection components 323c, the outer frame 323b and the suspension plate 323a. The piezoelectric element 323d is attached on the first surface of the suspension plate 323a and has a square structure. A length of a side of the piezoelectric element 323d is smaller than or equal to a length of a side of the suspension plate 323a. The suspension plate 323a has a bulge 323f disposed on a second surface thereof. The suspension plate 323a of the piezoelectric element 323 is disposed separately from the resonance plate 322 through the outlet frame 323b to form a chamber 327 among the suspension plate 323a of the piezoelectric actuator 323, the outlet frame 323b and the resonance plate 322. In addition, the first insulation plate 324, the conducting plate 325 and the second insulation plate 326 are stacked sequentially on the piezoelectric actuator 323.

By driving the actuator 223 to drive the gas transporting plate 221 to generate a resonance, the suspension plate 221b of the gas transporting plate 221 vibrates and displaces in a reciprocating manner, so as to make the air flow through the at least one vacant space 226 into the airflow chamber 217 and then discharged into the airflow channel 211 so as to achieve air transportation. The actions of the first gas transporting actuator 22 are described as follows.

Figure 5B:
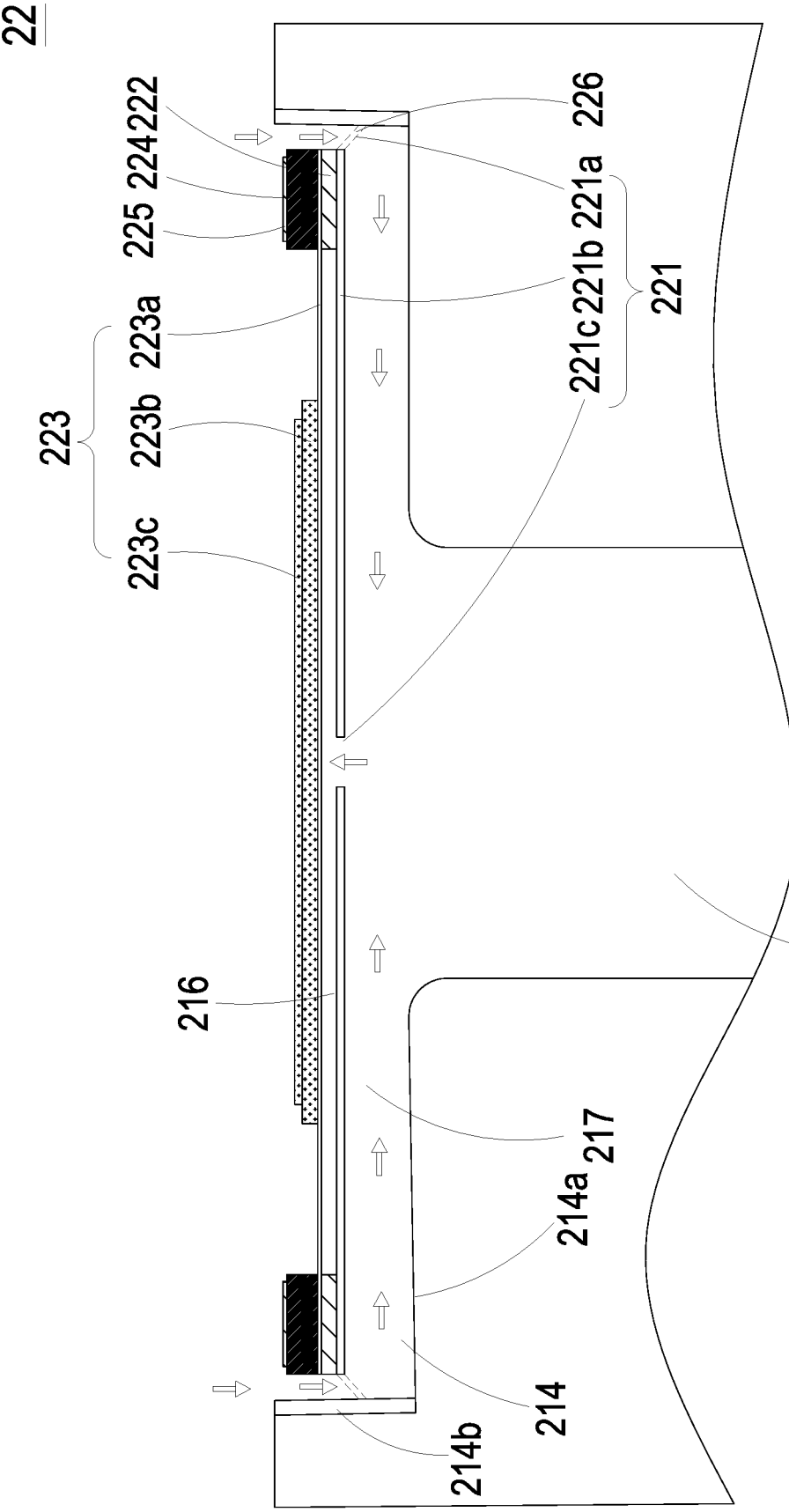
FIG. 5B and FIG. 5C are schematic views illustrating actions of the first gas transporting actuator of FIG. 5A.
Figure 5C:
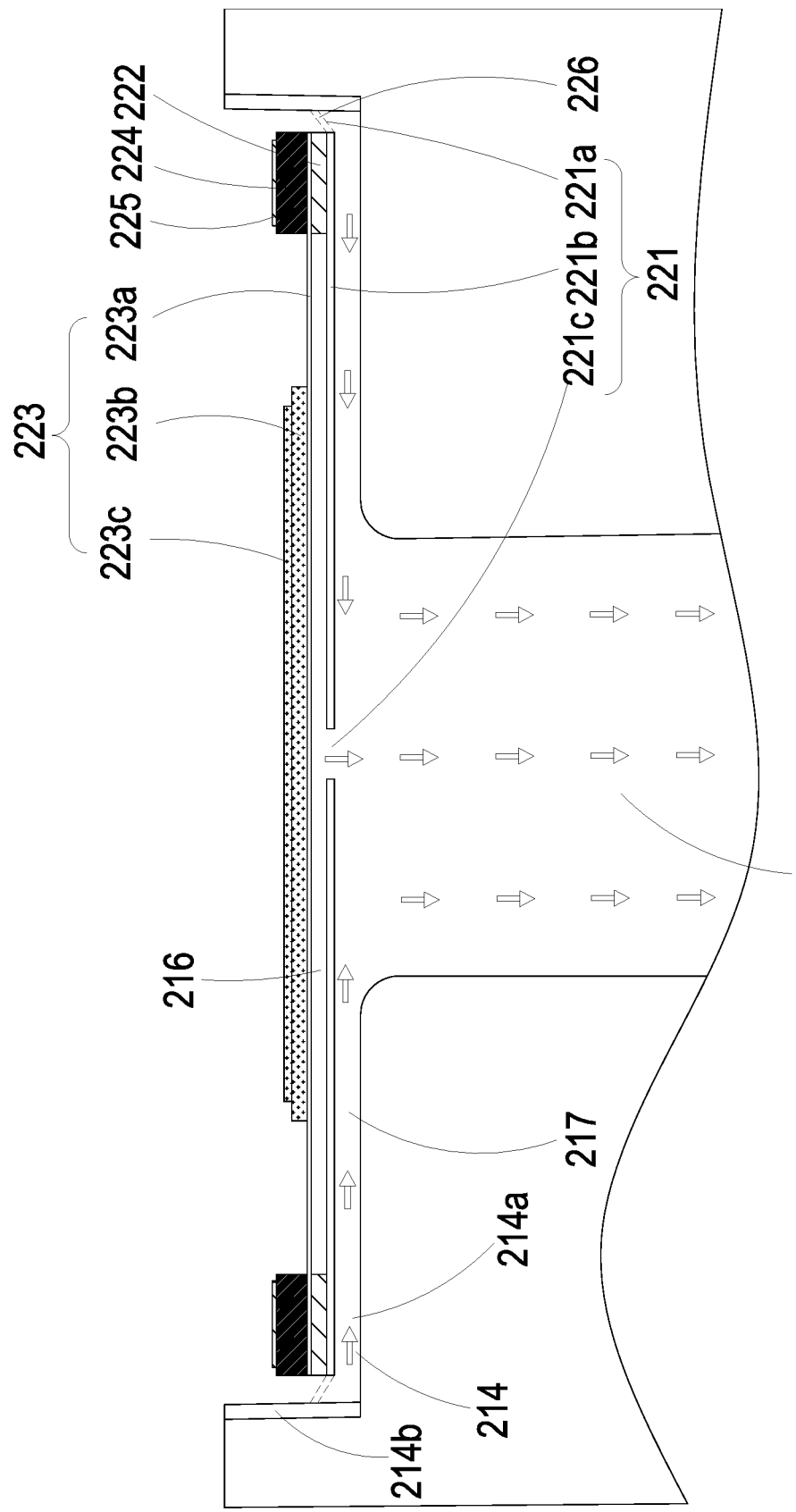

Please refer to FIGS. 5A to 5C. FIG. 5B and FIG. 5C are schematic views illustrating actions of the first gas transporting actuator of FIG. 5A. As shown in FIG. 5A, the first gas transporting actuator 22 is disposed within the accommodation slot 214 of the irradiating mechanism 21. The gas transporting plate 221 and the bottom surface 214a of the accommodation slot 214 are spaced apart from each other to form the airflow chamber 217 therebetween. As shown in FIG. 5B, when the piezoelectric plate 223c of the actuator 223 is actuated by an applied voltage, the piezoelectric plate 223c of the actuator 223 is deformed owing to the piezoelectric effect, and the adjusting resonance plate 233b and the piezoelectric carrying plate 233a are driven to vibrate in a reciprocating manner with a specific vibration frequency range. Thereby, the gas transporting plate 221 is driven to move due to the Helmholtz resonance effect and the actuator 223 is displaced upwardly. Since the actuator 223 is displaced upwardly, the volume of the airflow chamber 217 between the gas transporting plate 221 and the bottom surface 214a of the accommodation slot 214 is expended and the pressure in the airflow chamber 217 drops, by which a negative pressure forms therein. The negative pressure of the airflow chamber 217 inhales the air from the outside of the first gas transporting actuator 22 through the plurality of vacant spaces 226 among the plurality of brackets 221a of the gas transporting plate 221 and the lateral sides 214b of the accommodation slot 214, so that the pressure in the airflow chamber 217 increases to generate a pressure gradient. As shown in FIG. 5C, the air flows into the airflow chamber 217 continuously, and a positive pressure of the airflow chamber 217 is generated. Thus, the actuator 223 is driven to vibrate downwardly in response to the voltage and the volume of the airflow chamber 217 is shrunken and the air is pushed into the airflow channel 211. Consequently, the air is provided to the light sensing device 24 for measuring the concentration of the suspended particles contained in the air.

Figure 7:
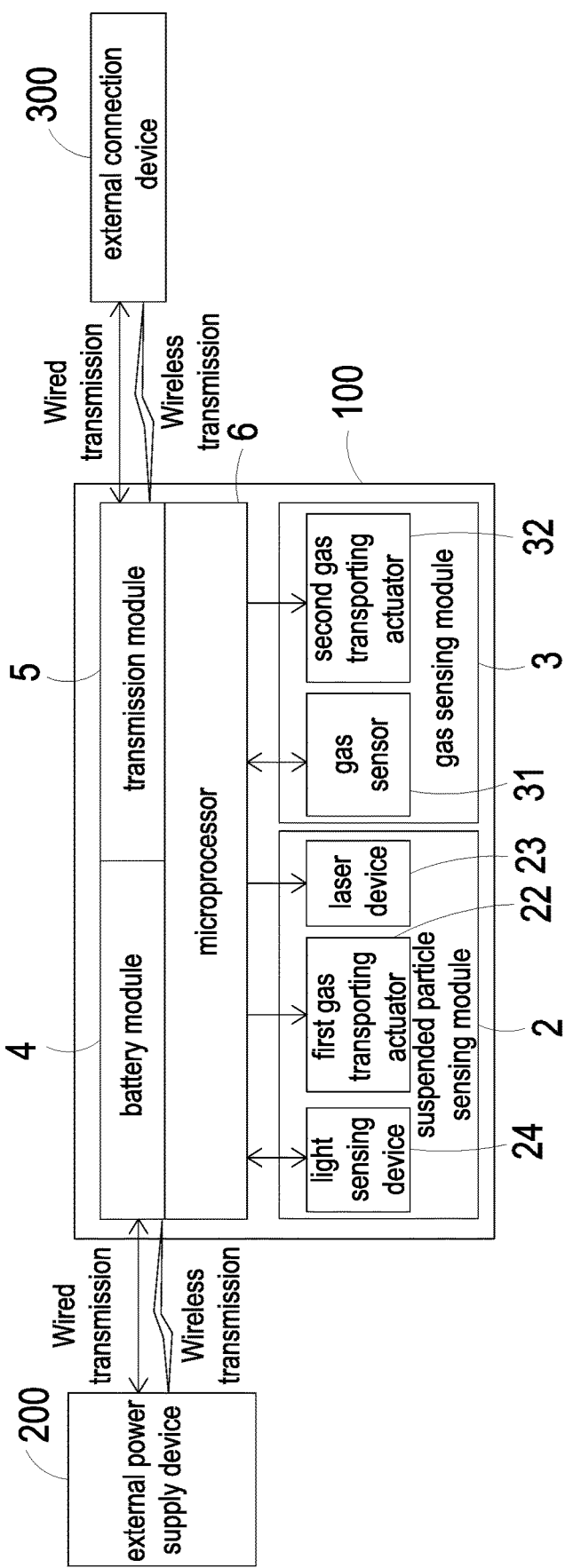
FIG. 7 is a block diagram of the gas detecting device of the present disclosure.

During the detection process of the suspended particle sensing module 2 or at a predetermined time point, the microprocessor (as shown in FIG. 7) drives the first gas transporting actuator 22 to introduce the air from the external environment through the first inlet 111 into the first gas transporting actuator 22 and the first gas transporting actuator 22 ejects the air at high speed to the airflow channel 211. Thereby, a cleaning operation is performed on a surface of the light sensing device 24 to remove the suspended particles attached thereon, so as to maintain accuracy of the light sensing device 24. The predetermined time point described above can be the time before performing the gas detection or a plurality of predetermined time points with a fixed time interval. For example, the cleaning operation is performed automatically every three minutes. The predetermined time point can be also controlled manually by the user or dynamically determined by the software based on the detected value calculated in real time. The present disclosure is not limited thereto.

Figure 6A:
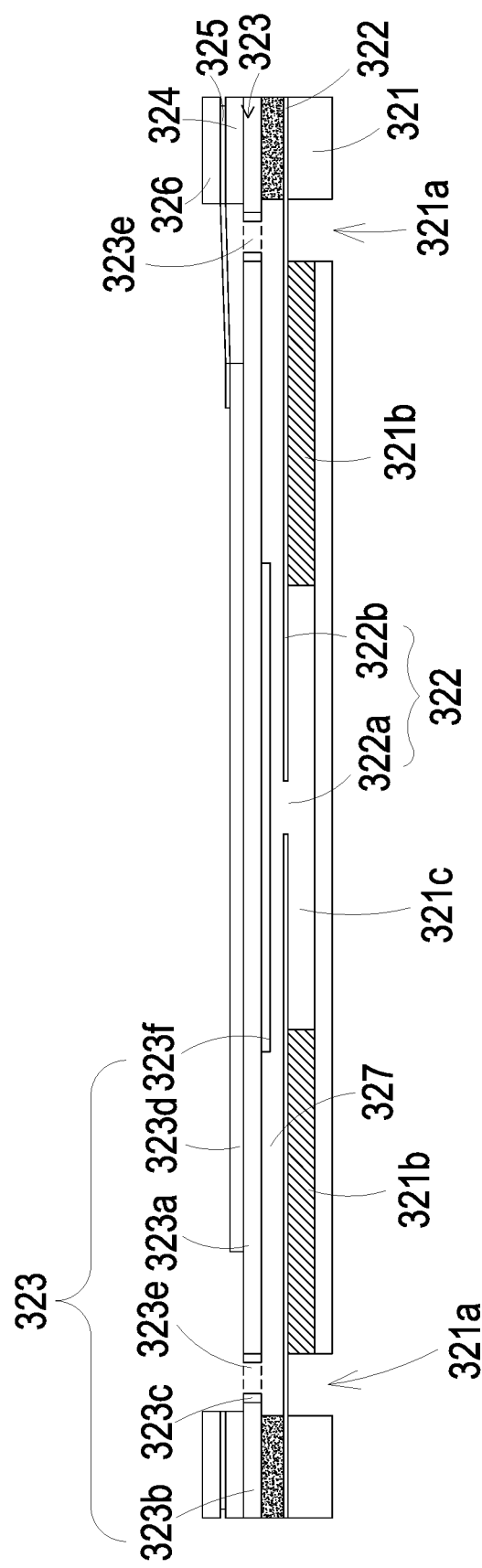
FIG. 6A is a schematic cross-sectional view illustrating the second gas transporting actuator of the present disclosure.
Figure 6B:
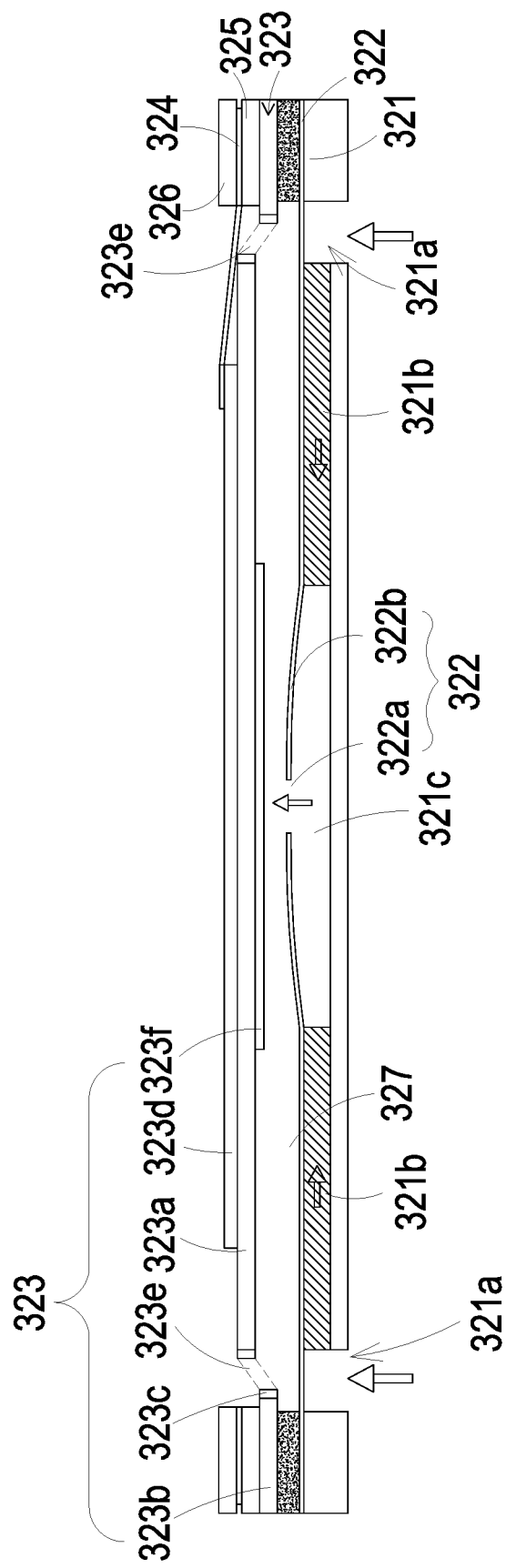
FIGS. 6B to 6D are schematic views illustrating actions of the second gas transporting actuator of FIG. 6A.
Figure 6C:
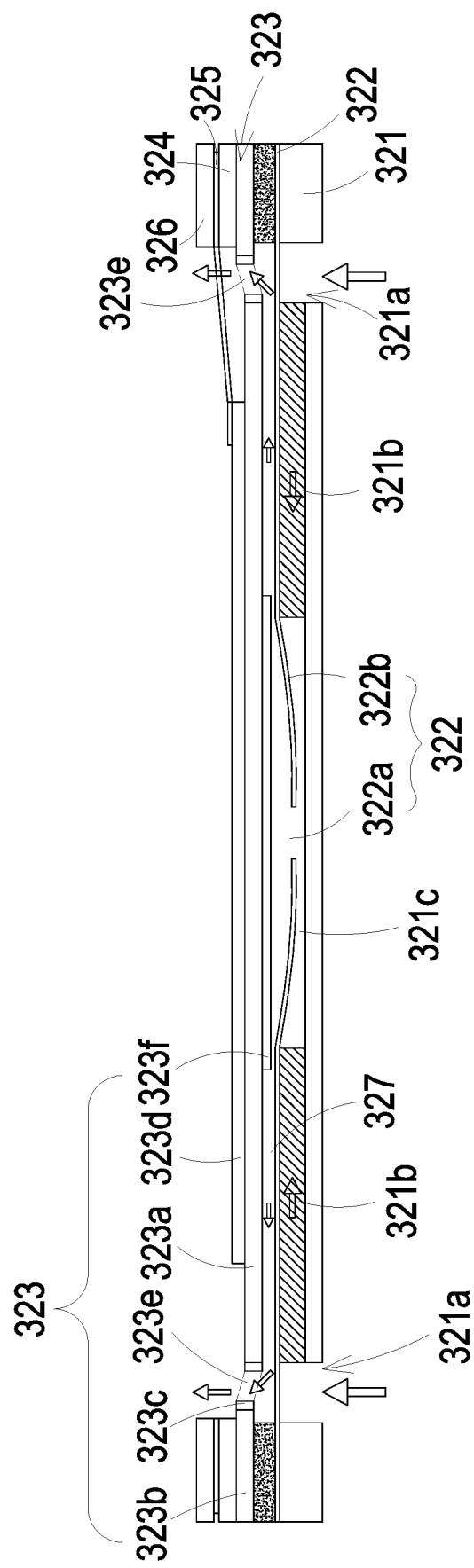
Figure 6D:
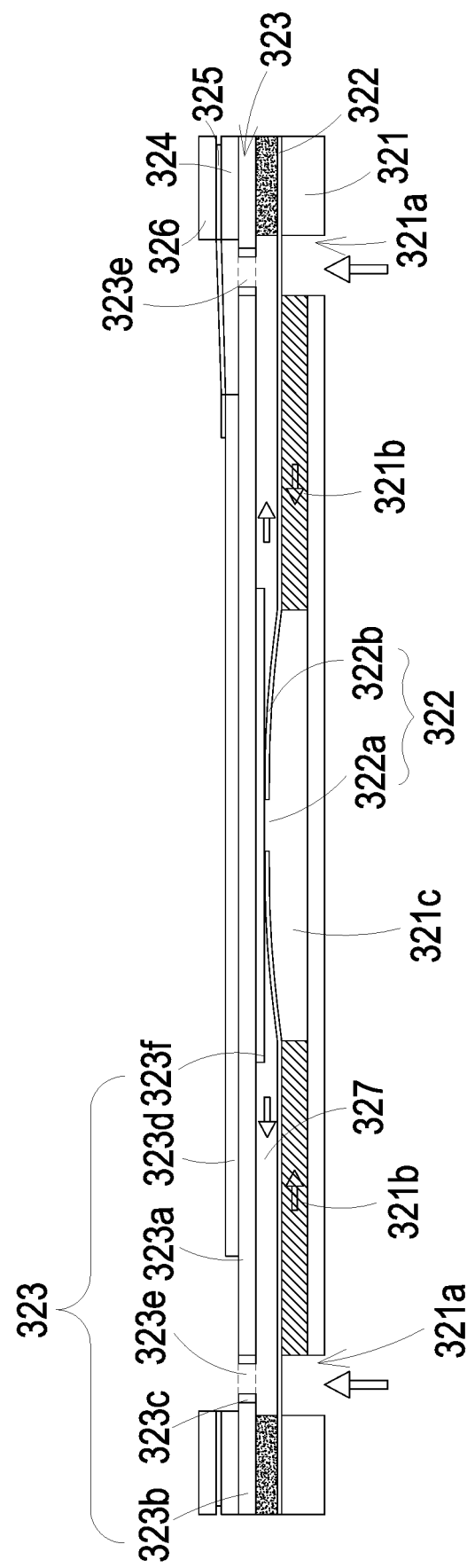

Please refer to FIGS. 6A to 6D. FIG. 6A is a schematic cross-sectional view illustrating the second gas transporting actuator of the present disclosure. The air inlet plate 321, the resonance plate 322, the piezoelectric actuator 323, the first insulation plate 324, the conducting plate 324 and the second insulation plate 326 of the second gas transporting actuator 32 are stacked and assembled sequentially. The resonance plate 322 and the suspension plate 323a of the piezoelectric actuator 323 are disposed separately to form a chamber 327 therebetween. FIGS. 6B to 6D are schematic views illustrating actions of the second gas transporting actuator of FIG. 6A. As shown in FIG. 6B, when the piezoelectric element 323d of the piezoelectric actuator 323 is actuated by an applied voltage, the piezoelectric element 323d is deformed owing to the piezoelectric effect, and the suspension plate 323a is driven to vibrate upwardly. Thereby, the movable part 322b of the resonance plate 322 is simultaneously driven to vibrate upwardly due to the Helmholtz resonance effect. Since the moveable part 322b is vibrate upwardly, the volume of the convergence chamber 321c is expended and the pressure in the convergence chamber 321c drops, by which a negative pressure forms therein. The negative pressure of the convergence chamber 321c inhales the air into the convergence chamber 321c through the inlet 321a. Please refer to FIG. 6C. The second gas transporting actuator 32 is continuously actuated and the suspension plate 323a of the piezoelectric actuator 323 is vibrate downwardly. Thereby, the movable part 322b of the resonance plate 322 is simultaneously driven to vibrate downwardly and the volume of the convergence chamber 321c is shrunken. The air is transported from the convergence chamber 321c to the chamber 327 formed between the piezoelectric actuator 323 and the resonance plate 322, pushed to the periphery by the bulge 323f of the suspension plate 323a, discharged out through the vacant space 323e. Finally, as shown in FIG. 6D, the suspension plate 232a is vibrated upwardly to the initial position and the volume of the chamber 327 is shrunken while the movable part 322b of the resonance plate 322 is displaced upwardly. The air is discharged through the periphery and the vacant space 323e. Since the volume of the convergence chamber 321c is expanded again, the air is inhaled through the inlet 321a continuously. Repeating the above actions, the air is inhaled through the inlet 321a and discharged though the vacant space 323e to achieve the gas transportation.

Please refer to FIG. 7. The gas detecting device 100 further includes a battery module 4 to provide the electrical energy and output the electrical energy to the suspended particle sensing module 2 and the gas sensing module 3. The battery module 4 may transmit the electrical energy via a wired transmission technology or a wireless transmission technology. Moreover, the battery module 4 is electrically connected to an external power supply device 200. The external power supply device 200 may continuously supply the battery module 4 with the electrical energy for storage. The external power supply device 200 can transmit the electrical energy to the battery module 4 by means of the wired transmission technology or transmit the electrical energy to the battery module 4 by the wireless transmission technology, but not limited thereto.

Please refer to FIG. 7. FIG. 7 is a block diagram of the gas detecting device of the present disclosure. The gas detecting device 100 further includes a transmission module 5 and a microprocessor 6. The microprocessor 6 is electrically connected to the battery module 4, the transmission module 5, the suspended particle sensing module 2 and the gas sensing module 3. The microprocessor 6 integrates the operation of the suspended particle sensing module 2 and the operation of the gas sensing module 3 together. The microprocessor 6 is used to drive the suspended particle sensing module 2 and the gas sensing module 3, and analyze, calculate and store detected results from the light sensing device 24 of the suspended particle sensing module 2 and the gas sensor 31 of the gas sensing module 3. When the microprocessor 6 enables the suspended particle sensing module 2, the first gas transporting actuator 22 is actuated to inhale the air and the air flows into the airflow channel 211. The air flowing into the airflow channel 211 is irradiated by the laser beam, which is emitted from the laser device 23 and passes through the light-beam channel 212. Thus, the light sensing device 24 detects scattered light spots generated by the suspended particles irradiated in air flowing in the airflow channel 211 and a detected result is transmitted to the microprocessor 6. According to the detected result, the microprocessor 6 analyzes the sizes of the suspended particles in the air, calculates the concentration of the suspended particles and thus generates a detected value accordingly. The detected value is stored in the microprocessor 6. Thereafter, the transmission module 5 transmits the detected value stored in the microprocessor 6 to an external connection device 300. The external connection device 300 can be one selected from the group consisting of a cloud system, a portable device and a computer system, so as to display the information carried by the detected value and issue a notification alert.

Moreover, when the microprocessor 6 enables the gas sensing module 3, the second gas transporting actuator 32 is actuated to inhale the air and the air is transported into the inlet channel 1231 through the second inlet 122. The air flowing into the inlet channel 1231 is detected by the gas sensor 31 disposed within the inlet channel 1231. The gas sensor 31 may measure the amount of one or more target gases therein. A detect result from the gas sensor 31 is transmitted to the microprocessor 6. The microprocessor 6 receives and analyzes the detected result from the gas sensor 31 to calculate the concentration of the target gases in the air and generate a detected value correspondingly. The detected value stored in the microprocessor 6 is transmitted to the external connection device 300 by the transmission module 5, so as to display the information carried by the detected value and issue a notification alert. The microprocessor 6 may also integrate the detected result from the suspended particle sensing module 2 with the detected result from the gas sensing module 3. The detected results are turned into an integrated value after processing by the microprocessor 6. Then, the microprocessor 6 may display such information carried by the integrated value via the external connection device 300.

In an embodiment, the transmission module 5 can be a wired transmission module and selected from the group consisting of a USB transmission module, a mini-USB transmission module and a micro-USB transmission module. In another embodiment, the transmission module can be a wireless transmission module and selected from the group consisting of a Wi-Fi transmission module, a. Bluetooth transmission module, a radio frequency identification transmission module and a near field communication transmission module.

In summary, the present disclosure provides a gas detecting device having a first sensing area and a second sensing area respectively. A suspended particle sensing module is disposed in the first sensing area and a gas sensor is disposed in the second sensing area. By using the first gas transporting actuator, the air is transported to flow toward the airflow channel. Then, the suspended particles contained in the air is irradiated by the laser beam to generate scattered light spots and the scattered light spots are detected by the light sensing device and the detected data are transmitted to the microprocessor. The microprocessor calculate concentrations of suspended particles PM2.5 and suspended particles PM10 in the air according to the detected data provided by the light sensing device. Moreover, the first gas transporting actuator is used to perform a cleaning operation on the light sensing device. In addition, the second gas transporting actuator disposed in the second sensing area is used to inhale the air into the inlet channel, and the gas sensor disposed in the inlet channel detects the air flowing through the inlet channel to measure the amount of a target gas contained in the air. The detected data are transmitted to the microprocessor. Accordingly, the gas detecting device of the present disclosure is provided to measure the gas concentration and the concentrations of suspended particles contained in the air at the same time.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A gas detecting device comprising:
    a main body having a first sensing area and a second sensing area, wherein the first sensing area has a first inlet and a first outlet disposed thereon, and the second sensing area has a second inlet and a second outlet;
    a suspended particle sensing module disposed in the first sensing area of the main body and comprising an irradiating mechanism, a first gas transporting actuator, a laser device and a light sensing device, wherein the first gas transporting actuator comprises a gas transporting plate, a chamber connection component, an actuator, an insulation connection component and a conducting connection component, wherein by driving the actuator to drive the gas transporting plate to generate a resonance, the suspension plate of the gas transporting plate vibrates and displaces in a reciprocating manner, so as to make the air flow discharged, so that the first gas transporting actuator transports air through the first inlet at high speed, suspended particles in the air are irradiated by laser beam emitted from the laser device to generate scattered light spots, and the scattered light spots are detected by the light sensing device to obtain sizes and a concentration of the suspended particles; and
    a gas sensing module disposed in the second sensing area of the main body and comprising a gas sensor and a second gas transporting actuator, wherein the second gas transporting actuator comprises an air inlet plate, a resonance plate and a piezoelectric actuator, wherein a chamber is formed between the resonance plate and the piezoelectric actuator, so that the air flows into the chamber when the piezoelectric actuator is driven, whereby the air is further transported through a resonance between the piezoelectric actuator and the movable part of the resonance plate, so that the second gas transporting actuator transports air through the second inlet at high speed, and the gas sensor detects the air to obtain a concentration of a target gas contained in the air.

2. The gas detecting device according to claim 1, wherein the irradiating mechanism is disposed in the first sensing area and comprises:
    an airflow channel in fluid communication with the first inlet and the first outlet;
    a light-beam channel crossing through the airflow channel;
    a light-source receiving slot in fluid communication with the airflow channel; and
    an accommodation slot disposed on one end of the airflow channel and aligned with the first inlet.

3. The gas detecting device according to claim 2, wherein the first gas transporting actuator is disposed within the accommodation slot of the irradiating mechanism and configured to inhale the air into the airflow channel.

4. The gas detecting device according to claim 2, wherein the laser device is disposed within the light-source receiving slot of the irradiating mechanism and configured to emit the laser beam into the light-beam channel.

5. The gas detecting device according to claim 2, wherein the light sensing device is disposed in the airflow channel and corresponding to a position under the light-beam channel, so that the light sensing device is aligned with the airflow channel and detects the scattered light spots of the suspended particles irritated by the laser device to calculate accordingly the sizes and the concentration of the suspended particles contained in the air.

6. The gas detecting device according to claim 2, wherein the accommodation slot of the irradiating mechanism comprises a plurality of fixing recesses.

7. The gas detecting device according to claim 6, wherein:
    the gas transporting plate having a plurality of brackets, a suspension plate and a central aperture, wherein the suspension plate is permitted to undergo a bending vibration, and the plurality of brackets are disposed in the plurality of fixing recesses so as to fasten the gas transporting plate in the accommodation slot, so that an airflow chamber is formed between the gas transporting plate and a bottom surface of the accommodation slot, and the plurality of brackets divide space between the suspension plate and the accommodation slot into at least one vacant space;
    the chamber connection component carried and stacked on the suspension plate;
    the actuator carried and stacked on the chamber connection component, wherein the actuator is configured to bend and vibrate in a reciprocating manner by an applied voltage;
    the insulation connection component carried and stacked on the actuator; and
    the conducting connection component carried and stacked on the insulation connection component;
    wherein a resonance chamber is defined by the actuator, the chamber connection component and the suspension plate collaboratively, wherein by driving the actuator to drive the gas transporting plate to generate a resonance, the suspension plate of the gas transporting plate vibrates and displaces in a reciprocating manner, so as to make the air flow through the at least one vacant space into the airflow chamber and then discharged into the airflow channel so as to achieve air transportation.

8. The gas detecting device according to claim 7, wherein each of the plurality of brackets has a fixing part and a connection part, wherein the fixing part and the fixing recess have shapes corresponding to each other, the connection part is connected between the suspension plate and the fixing part, and the connection part elastically supports the suspension plate for allowing the suspension plate to bend and vibrate in the reciprocating manner.

9. The gas detecting device according to claim 7, wherein the actuator comprises:
   a piezoelectric carrying plate carried and stacked on the chamber connection component;
   an adjusting resonance plate carried and stacked on the piezoelectric carrying plate; and
   a piezoelectric plate carried and stacked on the adjusting resonance plate, wherein the piezoelectric plate is configured to drive the piezoelectric carrying plate and the adjusting resonance plate to bend and vibrate in the reciprocating manner by the applied voltage, wherein the adjusting resonance plate is thicker than the piezoelectric carrying plate.

10. The gas detecting device according to claim 1, wherein the suspended particles detected by the light sensing sensor is one selected from the group consisting of suspended particles PM2.5, suspended particles PM10 and a combination thereof.

11. The gas detecting device according to claim 1, wherein the main body comprises a detecting chamber disposed within the second sensing area and the detecting chamber has an inlet channel and an outlet channel, wherein the inlet channel is aligned with the second inlet and the outlet channel is aligned with the second outlet, wherein the gas sensor is disposed on a bottom of the inlet channel, and the second gas transporting actuator is fixed within the detecting chamber and corresponding to the outlet channel.

12. The gas detecting device according to claim 1, wherein the gas sensor is at least one selected from the group consisting of an oxygen sensor, a carbon monoxide sensor, a carbon dioxide sensor, a bacterium sensor, a virus sensor, a microorganism sensor and combinations thereof.

13. The gas detecting device according to claim 1, wherein the gas sensor is a volatile organic compound sensor.

14. The gas detecting device according to claim 1, wherein:
   the air inlet plate having at least one inlet, at least one convergence channel and a convergence chamber, wherein at least one convergence channel is aligned with the at least one inlet, and the at least one inlet allows the air to flow in and the convergence channel guides the air from the inlet toward the convergence chamber;
   the resonance plate having a central aperture and a movable part, wherein the central aperture is aligned with the convergence chamber and the movable part surrounds the central aperture; and
   the piezoelectric actuator aligned with the resonance plate, wherein the chamber is formed between the resonance plate and the piezoelectric actuator, so that the air from the at least one inlet of the air inlet plate is converged to the convergence chamber along the at least one convergence channel and flows into the chamber through the central aperture of the resonance plate when the piezoelectric actuator is driven, whereby the air is further transported through a resonance between the piezoelectric actuator and the movable part of the resonance plate.

15. The gas detecting device according to claim 14, wherein the piezoelectric actuator comprises:
   a suspension plate being a square suspension plate, having a bulge, a first surface and a second surface and permitted to undergo a bending vibration;
   an outer frame arranged around the suspension plate;
   at least one connection component connected between the suspension plate and the outer frame for elastically supporting the suspension plate; and
   a piezoelectric element, wherein a length of a side of the piezoelectric element is smaller than or equal to a length of a side of the suspension plate, and the piezoelectric element is attached on the first surface of the suspension plate to drive the suspension plate to undergo the bending vibration in response to an applied voltage.

16. The gas detecting device according to claim 14, wherein the second gas transporting actuator comprises a conducting plate, a first insulation plate and a second insulation plate, and the air inlet plate, the resonance plate, the piezoelectric actuator, the first insulation plate, the conducting plate and the second insulation plate are stacked and assembled sequentially.

17. The gas detecting device according to claim 1, further comprising a battery module for storing electrical energy and providing electrical energy, wherein the battery module transmits the electrical energy by a means selected from the group consisting of a wired transmission technology and a wireless transmission technology, so that the electrical energy is provided to the suspended particle sensing module and the gas sensing device for actuation, measurement and operation, wherein the battery module is further electrically connected to an external power supply device, and the external power supply device supplies the electrical energy to the battery module for storage.

18. The gas detecting device according to claim 1, further comprising a microprocessor and a transmission module, wherein the microprocessor is used to analyze detected results from the suspended particle sensing module and the gas sensing device, and drive the first gas transporting actuator and the second gas transporting actuator, and the transmission module is used to receive and transmit signals, wherein the detected results from the suspended particle sensing module and the gas sensing device are analyzed and converted into detected values by the microprocessor, and the transmission module receives and transmits the detected values to an external connection device so that information carried by the detected values are displayed, stored and transmitted through the external connection device, wherein the external connection device is at least one selected from the group consisting of a cloud system, a portable device and a computer system.

19. The gas detecting device according to claim 18, wherein the transmission module is at least one selected from the group consisting of a wired transmission module and a wireless transmission module, wherein the wired transmission module is at least one selected from the group consisting of a USB transmission module, mini-USB transmission module, micro-USB transmission module, and the wireless transmission module is at least one selected from the group consisting of a Wi-Fi transmission module, a Bluetooth transmission module, a radio frequency identification transmission module and a near field communication transmission module.

* * * * *